United States Patent [19]

Sergeant

[11] Patent Number: 4,676,787
[45] Date of Patent: Jun. 30, 1987

[54] DIAPER

[75] Inventor: Timothy L. Sergeant, Seneca, S.C.

[73] Assignee: Gerber Products Company, Fremont, Mich.

[21] Appl. No.: 806,117

[22] Filed: Dec. 6, 1985

Related U.S. Application Data

[63] Continuation of Ser. No. 508,484, Jun. 27, 1983, abandoned.
[51] Int. Cl.⁴ ............................................. A61F 13/16
[52] U.S. Cl. .................................. 604/384; 604/385 R
[58] Field of Search ..................... 604/384, 385.1, 378

[56] References Cited

U.S. PATENT DOCUMENTS

| | | | |
|---|---|---|---|
| 2,860,637 | 11/1958 | Stamberger | 604/384 |
| 3,072,124 | 1/1963 | Jamison | 604/384 |
| 3,318,310 | 5/1967 | Pittendreigh et al. | 604/385 |
| 3,339,548 | 9/1967 | Seltzev | 604/385 |
| 3,395,706 | 7/1968 | Higgins et al. | 604/385 |
| 3,395,707 | 8/1968 | Whalen et al. | 604/385.1 |
| 3,602,224 | 8/1971 | Abre et al. | 604/385 |

FOREIGN PATENT DOCUMENTS

| | | | |
|---|---|---|---|
| 597804 | 5/1960 | Canada | 604/384 |
| 990901 | 6/1976 | Canada | 604/384 |

Primary Examiner—John D. Yasko
Attorney, Agent, or Firm—Townsend and Townsend

[57] ABSTRACT

A diaper is woven with an unfolded width of greater than about 40 inches, and is then folded along not fewer than three warp-direction fold lines in such a way that the central panel of the folded diaper includes at least four superposed layers while each side panel includes only one or two superposed layers. The number of filling yarns per inch in the diaper is considerably reduced, as compared to conventional diapers, thus providing an increase in production speed and hence a reduction in production cost, without decreasing (and generally increasing) the total thread count per square inch in, and absorbency of, the central panel.

12 Claims, 10 Drawing Figures

U.S. Patent    Jun. 30, 1987    4,676,787
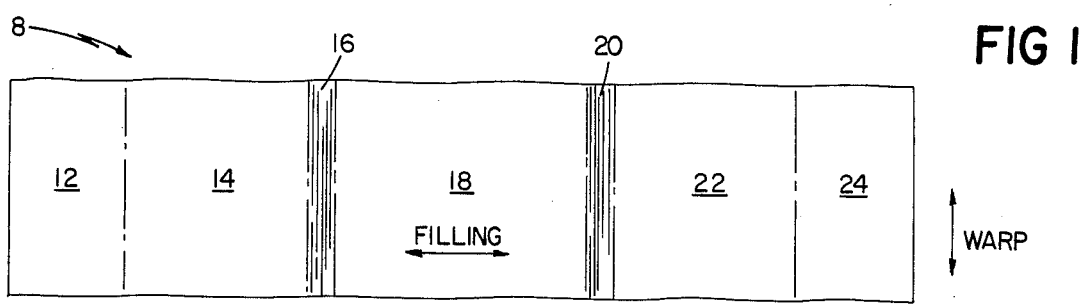
FIG 1
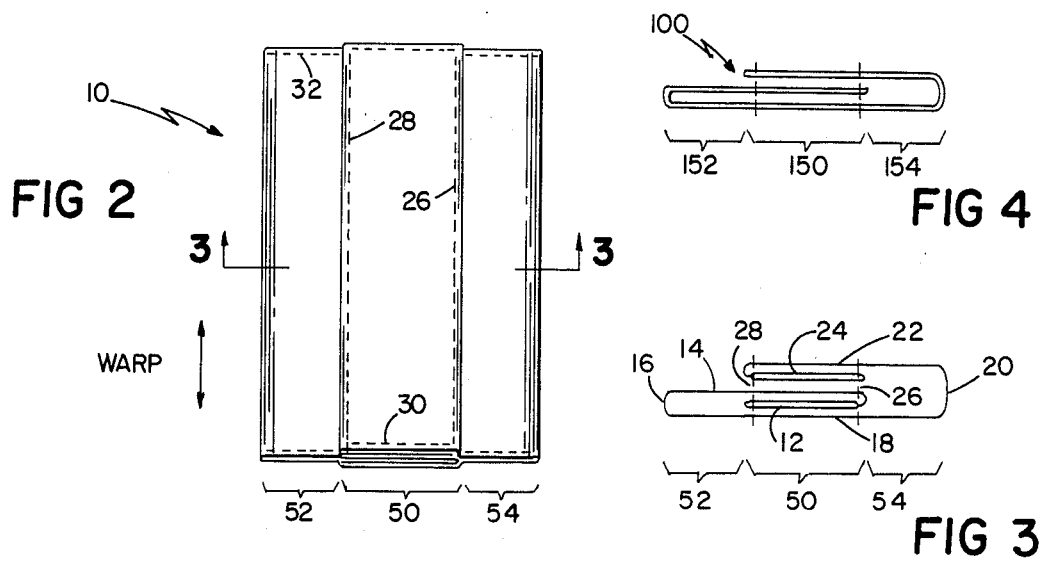
FIG 2
FIG 3
FIG 4
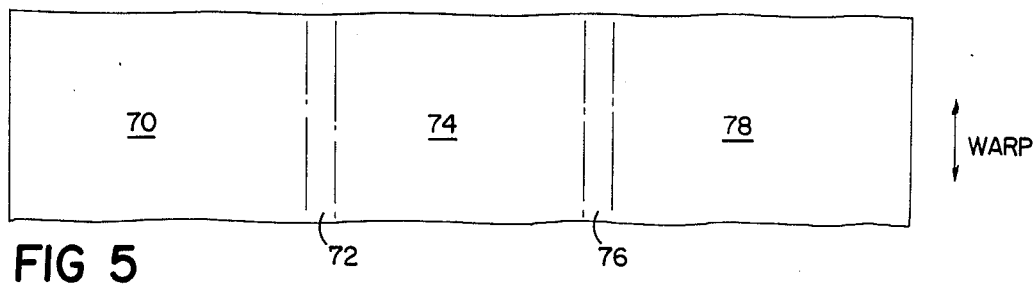
FIG 5
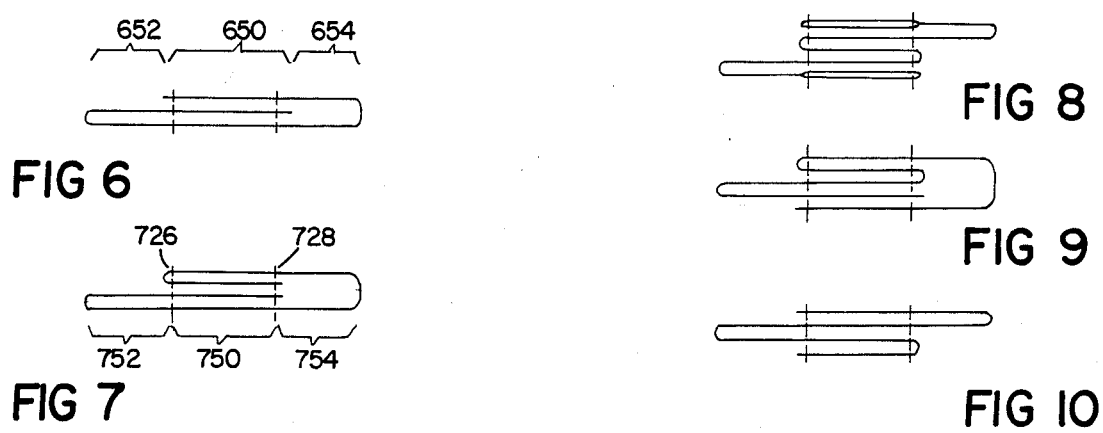
FIG 6
FIG 7
FIG 8
FIG 9
FIG 10

DIAPER

This a continuation of application Ser. No. 508,484 filed June 27, 1983, now abandoned.

FIELD OF THE INVENTION

This invention relates to fabric diapers and, more particularly, to pre-folded diapers.

BACKGROUND OF THE INVENTION

Conventional fabric diapers have been made from blanks woven in the form of a plurality of plies of a relatively light and open gauze diaper material, or as single plies of heavier diaper material utilizing special weave constructions to obtain the absorbency of the multi-ply diaper material. Generally, the width of the blank is between about 38 to 40 inches; and the blank is folded to form a finished diaper about 14½ to 15 inches wide. Normally, the diaper blank is folded transversly (i.e., along warpwise extending lines) to superimpose portions of its area to form three panels extending lengthwise of the diaper, i.e., a central panel which typically is about 5½ to 6½ inches wide and two side panels each of which is about 4 or 4½ inches wide. Typically, each side panel will include two layers of the blank (i.e., will be two blank layers thick) and the central panel will be three blank layers thick. Each blank layer may be either single or double-ply.

Examples of such prior diapers are shown in U.S. Pat. Nos. 2,845,069 to Jamison et al., 3,109,428 to Jamison, and 3,318,310 to Pittendreigh et al.

In the manufacture of such diapers, it is desirable to provide the good absorbency at low cost. Absorbency depends, among other things, on the number of plies and total thread count per square inch in the finished diaper (especially in the center panel), and generally can be increased by increasing the diaper bulk. On the other hand, increasing the bulk or amount of fabric in the diaper also will increase cost. Thus, it is generally expected that providing increased absorbency will result in a more expensive diaper, both to make and for the consumer.

SUMMARY OF THE INVENTION

The present invention provides a prefolded diaper that has better absorbency than a conventional diaper, and that nonetheless can be produced at less cost.

In particular, it has been discovered that if a diaper blank is made from fabric woven with an unfolded width of greater than about 40 inches, and is then folded along not fewer than three warp-direction fold lines in such a way that the central panel of the folded diaper includes at least four superposed blank layers while each edge panel includes only two superposed blank layers, the number of filling yarns in the diaper can be considerably reduced, with a corresponding increase in production speed and hence a reduction in production cost, all without decreasing (and generally increasing) the total thread count per square inch in, and absorbency of, the central panel.

Typically, the novel diaper of the present invention has fewer than 52 filling yarns per inch (and preferably in the range of 25-40 if the filling yarns have a weight of 20 Ne or lighter, and in the range of 20-30 if the weave is a birdseye or similar weave in which the filling yarn weight is heavier than 20 Ne), some of the superposed blanks layers in the center panel are woven double-ply rather than single ply (so that a center panel having, as in the preferred embodiment, five superposed blank layers will include six or more individual fabric plies,) the total thread count per square inch in the central panel is more than about 450, and the total thread count per square inch in each of the side panels is not more than about 300. The diaper blank has an unfolded width greater than 40 inches (and preferably about 48-50 inches) and a weight, without starch, in the range of about 3¾ to 4 yards per pound.

DESCRIPTION OF PREFERRED EMBODIMENTS

Some other objects, features and advantages of the present invention will appeal from the following detailed description of preferred embodiments thereof, taken together with the attached drawings in which:

FIG. 1 is a plan view of a diaper embodying the present invention, before folding;

FIG. 2 is a perspective view of the diaper of FIG. 1 after folding and stitching;

FIG. 3 is a section taken at 3—3 of FIG 2;

FIG. 4 is transverse sectional view of a conventional diaper;

FIG. 5 is a plan view of a second diaper embodying the present invention, before folding;

FIG. 6 is a simplified transverse sectional view illustrating the folding of a conventional birdseye woven diaper;

FIG. 7 is a simplified transverse sectional view illustrating the folding of a birdseye woven diaper embodying the present invention;

FIGS. 8-10 are simplified sectional views illustrating the folding of other diapers embodying the present invention.

Referring now to FIGS. 1-3, there is shown a multi-panel diaper, generally designated 10, made from a woven fabric blank 8. The fabric of the blank is woven in a 50 inch width from 24/1 (i.e., 24 Ne, single ply) cotton filling yarns and randomly alternating S and Z twist 31/1 (i.e., 31 Ne, single ply) cotton warp yarns. The direction of the warp and filling yarns is as indicated in FIGS. 1 and 2.

Across its transverse width, the fabric of blank 8 includes several different zones of different weave. Zones 12 and 24 are woven double ply in a plain weave. Zones 14, 16, 18, 20 and 22 are woven single ply in a 2/2 (or alternatively a 3.1 or a 3/2) twill weave. The other construction details of the different zones are as follows:

| Zone | No. of Warp Yarns/Inch | No. of Filling Yarns/Inch | Width of Zone |
|---|---|---|---|
| 12 | 49 (per ply) | 19 (per ply) | 6.2 in. |
| 14 | 66 | 38 | 9.6 in. |
| 16 | 98 | 38 | 1.5 in. |
| 18 | 66 | 38 | 13.1 in. |
| 20 | 98 | 38 | 9.6 in. |
| 22 | 66 | 38 | 6.2 in. |
| 24 | 49 (per ply) | 19 (per ply) | 6.2 in. |

After weaving, the fabric is bleached and dried, as is conventional, to provide a blank 48 inches wide. The bleached and dried blank 8 is then folded, as shown in FIGS. 2 and 3, forming a center panel (about 5½ in. wide and generally designated 50) including zones 12 and 24 and part of zones 14, 18 and 22, and two side sections (each about 4½ in. wide and generally designated 52 and 54, respectively) one of which includes zones 16 and part of zones 14 and 18 and the other of which includes zones 22 and part of zones 18 and 22. The folded blank is stitched along lines 26 and 28, thus securing the various panels together. As will be seen, zones 16 and 20 act as wear strips along the diaper edges. After cutting to 21 inch lengths (the typical length of a diaper) the transverse cut edges are secured by overedge stitching, as shown at 30 and 32 in FIG. 2, completing the prefolded diaper.

The advantages of the diaper of FIGS. 1 through 3 can best be appreciated by comparison to the conventional diaper, generally designated 100, shown in FIG. 4. The overall weights of the fabrics of diaper 100 and diaper 10 are about the same, about 3.8 to 3.9 yards per pound without starch.

Diaper 100 is made from fabric woven double ply. The top ply has 54 warp yarns/inch; the bottom ply has 36 warp yarns/inch; and there are 29 filling yarns per inch in each ply. The double-ply fabric thus has a total of 90 warp yarns and 58 filling yarns per inch. The width of the diaper blank after bleaching and drying is 36 inches and the blank is folded so that the center panel 150 of the diaper includes three superposed blank layers (a total of six plies) while each of the two side panels 152, 154 includes two superposed blank layers (a total of four plies). The total thread count per square inch in central panel 150 thus is 444, [(3(54+29))+(3(36+29))], while that in each of the side panels 152, 154 is 296. [(2(54+29))+(2(36+29))]. It thus will be seen that the total thread count per square inch in the central panel is fifty (50) percent greater than that in the side sections; and, since the total width of the side panels is about $4\frac{1}{2}$ inches while that of the center section is about $5\frac{1}{2}$ inches, about fifty (50) percent of the total diaper weight is in the center panel.

In diaper 10 of the present invention, center panel 50 includes five superposed blank layers (a total of seven plies), as follows:

| BLANK LAYER | THREAD COUNT PER IN.$^2$ |
|---|---|
| 14 | 66 + 38 = 104 |
| 12 | 2 (49 + 19) = 134 |
| 22 | 66 + 38 = 104 |
| 24 | 2 (49 + 19) = 134 |
| 18 | 66 + 38 = 104 |
| | Total (center panel 50) 580 |

Side panels 52, 54 each include two superposed blank layers:

| BLANK LAYER | THREAD COUNT PER IN.$^2$ |
|---|---|
| 14 or 22 | 66 + 38 = 104 |
| 18 | 66 + 38 = 104 |
| | Total (side panels 50, 52) 208 |

Since each side panel 50, 54 is about $4\frac{1}{2}$ inches wide while center panel 50 is about $5\frac{1}{2}$ inches wide, a little over 60% of the total weight of diaper 10 is in the center panel.

It thus will be seen that diaper 10 has both a greater percentage of its total weight and a higher total thread count per square inch in its center panel than does diaper 100. Strike-through tests show also that diaper 10 has significantly better absorbency than does diaper 100. Such tests are conducted by cutting 4 inch diameter samples from the center panels of the respective diapers, placing the samples over a funnel, and then applying 40 milliliters of water (typically from a calibrated burrett) to the sample over the funnel. The total amount of water that passes (i.e., "strikes") through the cut-out samples is collected and measured. It has been found that an average of 8.75 milliliters (of the total 40 ml. applied from the burrett) strikes through cut-out samples from diaper 10, while about twice as much (an average of 17.0 ml. of the total 40 ml. applied) strikes through the cut-out samples from the conventional diaper 100. Based on these tests, the diaper 10 constructed in accord with the present invention is expected to be about 50% more absorbent than a conventional diaper such as diaper 100.

The diaper 10 of the present invention is also more economical to manufacture. The two diapers, and the fabrics from which the respective diaper blanks are made, have about the same overall weight. However, because the diaper fabric of the present invention requires only 38 filling yarns per inch, as contrasted with the 58 filling yarns per inch of the conventional diaper fabric, the production rate of fabric for diaper 10 is about 50% greater than that of fabric for conventional diaper 100.

OTHER EMBODIMENTS

In other embodiments of the invention, other thread counts and weaves may be employed. The following are exemplary.

EXAMPLE I

A single layer diaper fabric having a thread count of 78 warp yarns per inch and 35 filling yarns per inch may be woven from 31/1 warp yarns and 27/1 filling yarns. If such a fabric is woven 50 inches wide, dried to provide a blank of 48 inch width and than folded as shown in FIGS. 2 and 3, the resulting diaper will have a total thread count of 565 threads per square inch in its center panel (which is 5 blank layers thick) and 226 threads per square inch in its two side panels. Such a diaper will have about the same total weight as diaper 100, but can be made at an approximately 55% higher production rate.

EXAMPLE II

Diaper fabric having the five-zone construction shown in FIG. 5 was woven in a 50 inch width from 27/1 cotton filling yarn and a 50/50 mixture of randomly alternating S and Z twist 31/1 cotton warp yarns. All zones were woven single ply, 34 picks per inch; and the various zones had the following additional construction details:

| Zone | Weave | No. of Warps Yarns/Inch | Approx. Width of Zone |
|---|---|---|---|
| 70 | 2/1 twill | 72 | $16\frac{1}{2}$ in. |
| 72 | cord | 96 | $1\frac{1}{2}$ in. |
| 74 | 2/1 twill | 72 | 14 inches |
| 76 | cord | 96 | $1\frac{1}{2}$ in. |
| 78 | 2/1 twill | 72 | $16\frac{1}{2}$ in. |

After bleaching, the fabric was dried to provide a 48 inch wide blank; and the blank was folded and stitched in the manner shown in FIGS. 2 and 3 to secure the blank layers together, and cut to 21 inch lengths. Overedge stitching was applied to the cut ends, as shown in FIG. 3. Zones 72 and 76 formed wear strips along the diaper's side edges.

The resulting diaper had a total thread count of 212 per square inch in its side panels (both of which are two blank layers thick, and one of which includes portions of zones 70 and 74 and the other of which includes portions of zones 74 and 78) and 530 per square inch in its center panel (which is five blank layers thick and includes portions of zones 70, 74 and 78). The production rate for the fabric from which the diaper is made is about 50 percent greater than that of the conventional fabric for diaper 100.

EXAMPLE III

Diaper fabric of zoned construction, including seven zones of the same respective widths as zones 12 through 24 of diaper 10 was woven in a 50 inch width using 27/1 cotton filling yarns and 31/1 cotton warp yarns. Other construction details of the various zones (identified by the same number as the corresponding zones of diaper 10 but adding a differentiating prime, are as follows:

| Zone | No. of Warp Yarns/Inch | No. of Filling Yarns/Inch | Weave |
|---|---|---|---|
| 12' | 51 (per ply) | 17 (per ply) | plain, double ply |
| 14' | 62 | 33 | 3/1 twill |
| 16' | 82 | 33 | 3/1 twill |
| 18' | 62 | 33 | 3/1 twill |
| 20' | 82 | 33 | 3/1 twill |
| 22' | 62 | 33 | 3/1 twill |
| 24' | 51 (per ply) | 17 (per ply) | plain, double ply |

After bleaching, the fabric was dried at a 48 inch width, and the resulting blank was folded as in FIG. 2 and stitched along the seam lines corresponding to lines 26 and 28 to secure the blank layers together. After cutting to 21 inch lengths, the cut edges were secured by overedge stitching, in the manner shown in FIG. 3. The resulting diaper had good absorbency values and a production rate over 50% greater than that of diaper 10.

EXAMPLE IV

A diaper fabric was woven in the same manner as the diaper of Example III, except that the zones corresponding to zones 12', 18' and 24' were woven in a honeycomb weave construction. The resulting diaper had good absorbency.

EXAMPLE V

A diaper fabric was woven, 50 inches wide in a single layer 2/2 broken twill weave; and the fabric was then bleached, dried, folded, cut and stitched in the same manner as described with reference to diaper 10. The resulting diaper had good absorbency.

EXAMPLES VI and VII

Two diaper fabrics were produced in a 50 inch width using 15/1 cotton filling yarns and 31/1 cotton warp yarns. One fabric was woven in a 3-float birdseye weave; the other in a 3-float diamond weave. Both weaves were produced using approximately 56 warp yarns per inch and 22 filling yarns per inch.

After bleaching, the fabrics were dried at 48 inch wide; and the resulting blanks were folded and stitched as in FIG. 2, and then cut to 21 inch length and overedge stitched along the cut edges as shown in FIG 3. Diapers made from the diamond weave fabric are expected to have better integrity than those from the birdseye weave. Both diaper fabrics have a greater production rate than conventional birdseye diapers, and can be expected to have significantly better absorbency than a conventional birdseye diaper. A conventional birdseye diaper typically is made from a single ply fabric, woven with 31/1 warp yarns (56 yarns per inch) and 12/1 filling yarns (28 yarns per inch) and folded (as shown in FIG. 6) so as to produce a central panel 650 that is 3 blank layers thick and side panels 652 and 654 each of which is two blank layers thick.

Example VIII

Diaper fabric was produced in a 44 inch width, using 11.3/1 cotton filling yarns and 31/1 cotton warp yarns to produce a 3-float birdseye weave having approximately 50 warp yarns per inch and 28 filling yarns per inch. After bleaching, the fabric was dried to provide a 42 inch wide blank that was then folded as shown in FIG. 7 to provide a diaper having a center panel 750 that is 4 blank layers thick and side panels 752, 754 that are each 2 blank layers thick. The folded blanks were stitched along lines 726, 728 to secure the folded layers together, and then cut to 21 inch lengths. The cut edges were seamed by overedge stitching, in the same manner as shown in FIG. 3 with respect to diaper 10. Strikethrough testing showed that the diaper of Example VIII was about 30 percent more absorbent (an average strikethrough of 15.5 milliliters of water as compared to 22 milliliters) in its center panel than a conventional birdseye diaper.

As will be apparent, diaper fabrics made in accord with the present invention may be folded in several ways other than as shown in, for example, FIGS. 2 and 7.

FIGS. 8 and 9 illustrate two further ways that 50 inch wide (dried to 48 inch) fabric may be folded. As is evident, the diapers shown in each of FIGS. 8–9 include center panels that are 5 blank layers thick (there are a total of 7 plies in the center panel of the diaper of FIG. 8 in which, as in diaper 10, the end zones are woven double-layer) and side panels that are 2 blank layers thick.

FIG. 10 illustrates another way in which 44 inch wide (dried to 42 inch wide) birdseye woven fabric may be folded to provide, as in the diaper of FIG. 7, four blank layers in the center panel and two blank layers in each of the side panels.

Other embodiments will be within the scope of the following claims.

What is claimed is:

1. A diaper prefolded from a blank of woven fabric so as to have a five layer, central panel and a pair of two layer side panels, the improvement comprising said blank being folded to one side of the plane thereof, along four fold lines extending warp-wise of the fabric to provide five zones, said zones including edge zones of double ply material and three intermediate zones of single ply material, said blank being further characterized by the number of filling yarns per inch being the same in each of said five zones, and the folding of said blank being so as to position said double ply edge zones internally of said prefolded diaper.

2. The prefolded diaper of claim 1 wherein the total thread count per square inch in each of said side panels is less than about 300.

3. The prefolded diaper of claim 1 wherein said filling yarns have a weight lighter than 20 Ne and said weave comprises not less than 25 filling yarns per inch.

4. The prefolded diaper of claim 1 wherein said blank comprises a birdseye weave having in the range of 20 to 30 filling yarns per inch.

5. The prefolded diaper of claim 1 wherein weave includes in the range of 25 to 40 filling yarns per inch in each layer of said blank.

6. The prefolded diaper of claim 1 wherein said two of said zones have a greater number of warp yarns per inch than the other of said zones and being positioned intermediate adjacent ones of said other of said zones.

7. The prefolded diaper of claim 1 wherein said blank includes at least seven transversely-spaced zones.

8. The prefolded diaper of claim 1 wherein said central panel comprises at least a portion of each of said other of said zones and each of said side panels comprises at least a portion of each of two of said other of said zones.

9. The diaper of claim 1 wherein each of said zones has not more than 40 filling yarns per inch.

10. The prefolded diaper of claim 1 wherein the width of said blank is not less than about 48 inches.

11. The prefolded diaper of claim 1 wherein the total thread count per square inch in said center panel is not less than 500.

12. The prefolded diaper of claim 1 wherein said fabric has a weight, without starch, in the range of about $3\frac{3}{4}$ to 4 yards per pound.

* * * * *